United States Patent
Crooks et al.

(10) Patent No.: US 7,341,981 B2
(45) Date of Patent: Mar. 11, 2008

(54) SPRAY COMPOSITION HAVING A DEPOSITION CONTROL AGENT

(75) Inventors: Regan Crooks, Hightstown, NJ (US); Justin Cooper-White, Queensland (AU); Valerie Roux-Jallet, Biviers (FR); Francis George Smith, Robbinsville, NJ (US); Andrew Douglass, East Windsor, NJ (US); Joel M. Coret, Robbinsville, NJ (US)

(73) Assignee: Rhodia Inc., Cranbury, NJ (US)

( * ) Notice: Subject to any disclaimer, the term of this patent is extended or adjusted under 35 U.S.C. 154(b) by 0 days.

(21) Appl. No.: 11/174,065

(22) Filed: Jul. 1, 2005

(65) Prior Publication Data

US 2006/0105928 A1    May 18, 2006

(51) Int. Cl.
   *C11D 1/00*     (2006.01)
   *C11D 3/22*     (2006.01)
   *C08B 37/00*    (2006.01)
   *A61K 31/715*   (2006.01)
   *A01N 43/00*    (2006.01)

(52) U.S. Cl. .................. 510/199; 510/470; 523/122; 536/114; 536/123.1; 514/54

(58) Field of Classification Search .............. 510/199, 510/470; 523/122; 536/114, 123.1; 514/54
   See application file for complete search history.

(56) References Cited

U.S. PATENT DOCUMENTS

| | | | |
|---|---|---|---|
| 3,483,121 A | 12/1969 | Jordan | 252/8.55 |
| 3,498,912 A | 3/1970 | Kieper et al. | 210/49 |
| 3,723,408 A | 3/1973 | Nordgren et al. | 260/209 R |
| 3,723,409 A | 3/1973 | Yueh | 260/209 R |
| 3,740,388 A | 6/1973 | Montgomery et al. | 260/209 R |
| 5,824,797 A * | 10/1998 | Hazen | 536/114 |
| 6,534,563 B1 | 3/2003 | Bergeron et al. | 523/122 |

* cited by examiner

*Primary Examiner*—Brian Mruk

(57) ABSTRACT

A spray composition includes an aqueous spray medium, an active ingredient, and a deposition control agent, wherein:
   the composition comprises at least one surfactant, and
   the deposition control agent is selected from the group consisting of the following:
      hydroxypropyl guar having a molecular substitution of at least 0.6,
      hydroxyalkyl guars, wherein the alkyl has at least 4 carbon atoms, having a molecular substitution of at least 0.15,
      guar having both carboxymethyl groups and hydoxyalkyl groups and having a molecular substitution of at least 0.1, and
      guar having both hydroxyalkyltrimethylammonium,
   preferably hydroxypropyltrimethylammonium or alkyltrimethylammonium and hydroxyalkyl groups.

15 Claims, 6 Drawing Sheets

Comparison of Guars all with 0.1wt% anionic phosester, and the anionic phosester alone at a pH of 5, and drop diameters of 2,1mm impacting at 3m/s

SPRAY COMPOSITION HAVING A DEPOSITION CONTROL AGENT

FIELD OF THE INVENTION

The invention relates to spray compositions having an aqueous spray medium, an active ingredient, and a deposition control agent. The inventions relates more particularly to improvements of such compositions when they comprise a surfactant.

BACKGROUND OF THE INVENTION

A spray composition is used for delivering an active ingredient onto a target, in the form of droplets. The composition is spayed (forming droplets), by using appropriate means, and the droplets encounter the target. This is used for example for applying an agrochemical on a field. Spraying means are typically mounted on aircraft, tractors, ground rigs, irrigation systems or railcars. A spray may also be dispensed from a canister by mechanical (e.g. pump) or chemical (e.g. propellant) means. A spray composition comprises an aqueous spray medium and the active, dispersed therein, in a solid form or liquid form, optionally in a solution form in an aqueous medium or in a further solvent. Spraying is also used for applying a coating composition onto a surface. This includes, for example, industrial paints, coil-coatings, paper, or film coatings.

In order to improve the deposition of the active ingredient on the target, and thereby in order to improve the efficacy of the spraying, the use of deposition aid agents is known. Deposition aid agents include:

- drift-control agents: agents avoiding the droplets to miss the target area, and thus permitting reduction of the amount of active ingredient, which in turn reduces economical and environmental concerns,
- anti-bouncing agents: agents avoiding rebound or splashing of the droplet when said droplet meets the target, for example a leaf, and thus reducing loss of active ingredient to the ground, which in turn reduces economical and environmental concern,
- anti-leaching agents or rain-fastness agents: agents avoiding the composition to be removed from the target by rain or wind, after deposition of composition onto the target, and/or allowing a long lasting effect of the active, which in turn reduces economical and environmental concerns, and
- anti-misting agents.

Known drift-control agents include polyacrylamides, polyethylene oxides, and polyvinylpyrrolidone.

Document U.S. Pat. No. 5,824,797 describes using some guar compounds as drift-control agents and as bioefficacy enhancers, in agricultural spray compositions. Document U.S. Pat. No. 6,534,563 describes using some guars as anti-rebound agents in agricultural spray compositions. Compound Jaguar 8000, a hydroxypropyl guar having a molecular substitution of about 0.4 is used as a drift reducer in agricultural spray compositions.

There is a need in providing new spray compositions.

BRIEF SUMMARY OF THE INVENTION

The invention relates to new spray compositions. Thus, the invention relates to a spray composition having an aqueous spray medium, an active ingredient, and a deposition control agent, wherein:

the composition comprises at least one surfactant, and
the deposition control agent is selected from the group consisting of the following:

- hydroxypropyl guar having a molecular substitution of at least 0.6, preferably of at least 0.8, more preferably of at least 1.1, and even more preferably of at least 1.3,
- hydroxyalkyl guars, wherein the alkyl has at least 4 carbon atoms, having a molecular substitution of at least 0.15,
- guar having both carboxymethyl groups and hydoxyalkyl groups, preferably carboxymethyl-hydroxypropyl guar, having a molecular substitution of at least 0.1
- guar having both hydroxyalkyltrimethylammonium, preferably hydroxypropyltrimethylammonium or
- alkyltrimethylammonium and hydroxyalkyl, preferably hydroxypropyl, groups, the total molecular substitution being preferably of at least 0.1.

The composition presents improved deposition properties in the presence of the surfactant.

The invention also relates to a method of controlling the deposition of a composition comprising an active agent, comprising the step of:

preparing a spray composition according to one of the preceding claims, and
ground or aerial spraying or discharging droplets of the composition.

The improved and/or controlled deposition properties relate to drift-control and/or anti-rebound and/or anti-leaching and/or anti-misting properties.

DETAILED DESCRIPTION OF THE INVENTION

Definitions

In the present specification, the term "molecular substitution" ("ms") refers to the number of derivatizing groups per monosaccharide unit of the guar. This is a parameter relating to the derivatizing groups. The molecular substitution can be determined by the Zeisel-GC method, based on the following literature reference: K. L. Hodges, *W. E. Kester, D. L. Wiederrich, and J. A. Grover, "*Determination of Alkoxyl Substitution in Cellulose Ethers by Zeisel-Gas Chromatography*", Analytical Chemistry, Vol. 51, No. 13, November 1979. When using this method the following gas chromatograph conditions can be used:

Column: DB-1 (30 m×0.32 mm ID×1.0 µm film thickness),
Program: 75 degrees Celsius-300 degrees Celsius at 25 degrees ° C./min (hold at 75° C. for 5 minutes),
Detector: Flame Ionization,
Injector/Detector Temperature: 250/320° C., Carrier gas Flow: Helium—~1 ml/min,
Split flow: Helium—20 ml/min, and
Injection volume: 1 microliter.

In the present specification, the term "degree of substitution" ("ds") refers to the number of hydroxyl groups of the guar substituted with the derivatizing groups, per monosaccharide unit of the guar. This is a parameter relating to the derivatized sites.

An example of the definitions of ms and ds is given in the figure

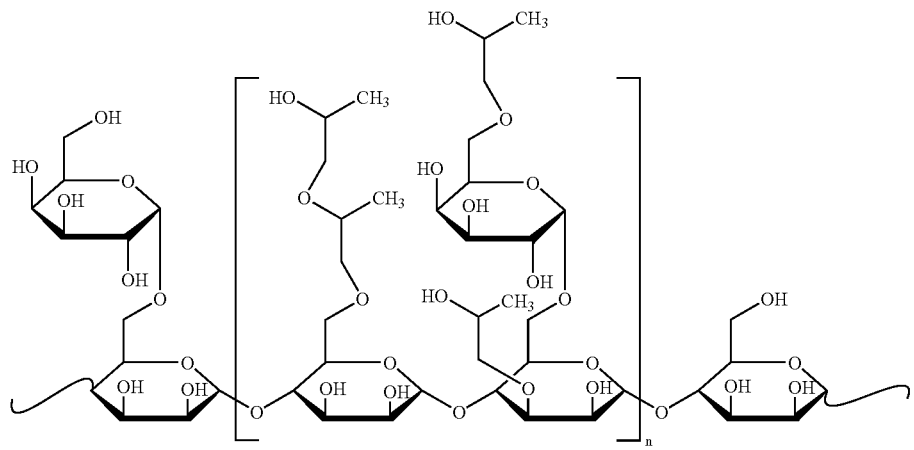

For this hydroxypropyl guar, ms=4/3=1.33 and ds=3/3=1.

In the present specification, the term "molecular weight" of the deposition control agent refers to the weight average molecular weight measured using Gas Permeation Chromatography. This can be measured with the following:
- column and mobile phase: Supelco Progel TSK G3000PW$_{XL}$ in series with a mobile phase of 100 mM NaNO$_3$ and 0.02% NaN$_3$,
- detector used was a Waters 410 Refractive Index detector,
- the samples are dissolved in the mobile phase to give 0.025% solutions by weight and filtered through a 0.45 micron filter prior to injection, and
- the calibration curve is generated using stachyose and 2 guar samples of molecular weights of 667, 58,000 and 200,000 grams per mole ("g/mol").

Characteristics of Drops or Rebounds

Figure 1:
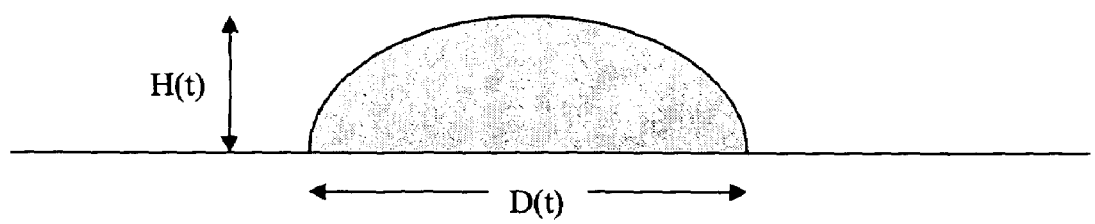
FIG. 1 illustrates a drop on a surface and the characteristics describing the drop impact.

The characteristics of the drop are described using the following parameters:
- "D0"—initial drop diameter. This is the diameter of the drop before impacting the surface (units of mm). This is measured from images taken by the camera;
- "D(t)"—this is the diameter of the drop on the surface during spreading and recoil when impacting the surface or after, as shown in FIG. 1 (units of mm). This measured from images taken by the camera;
- "H(t)"—this is the height of the drop measured from the surface during spreading and recoil when impacting the surface or after, as shown in FIG. 1 (units of mm). This is measured from images taken by the camera; and
- time (ms)—the time measured from the moment of the drop impacting the surface in terms of milliseconds. This corresponds to the frame rate of the camera used to capture the images.

Figure 2:
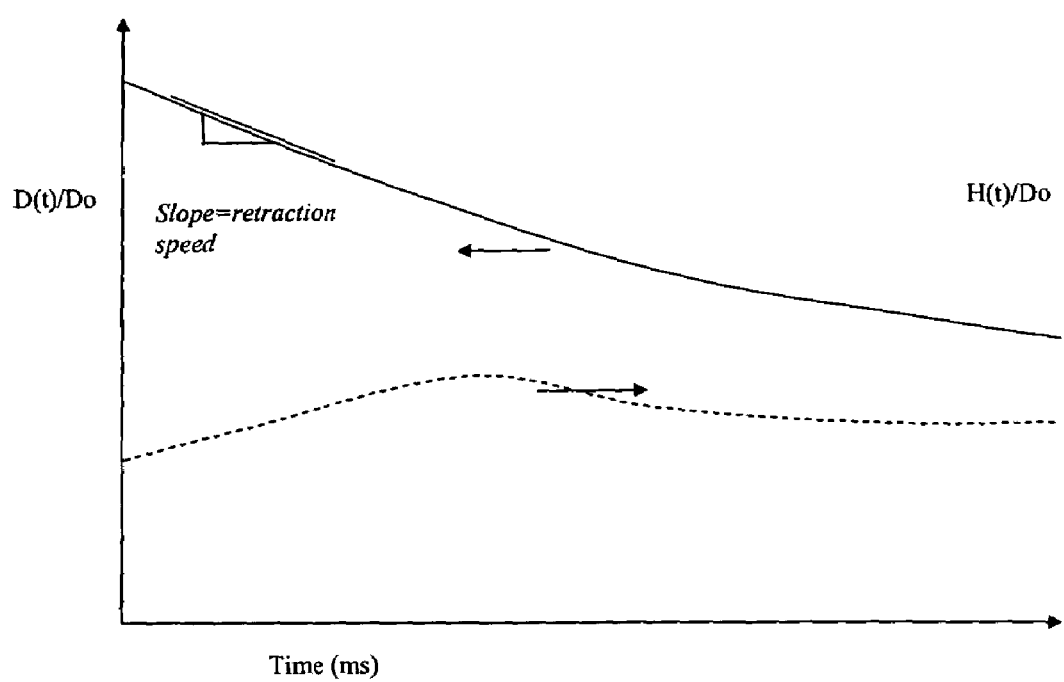
FIG. 2 illustrates the determination of drop retraction speed.

The "retraction speed" of the drop impacting the surface is defined as the slope of D(t)/D0 as a function of time, taken from the maximum in D(t)/D0, typically at 2 ms in the results presented here, until 10 ms, as shown in FIG. 2. The lower the retraction speed is, the better the deposition control is (for example for anti-bouncing properties).

Images are captured using a high speed camera Phantom 5 Science Technology that allows variation in the frame capture rate. This capture rate is varied according to the speed of impact of the drop, typically at 3 m/s impact a frame rate of 1000 frames/sec is used. A 10 ml syringe is filled and connected to a pump; the solution is pushed at 1 to 3 ml/h through silicon tubing equipped with a needle of 0.38 mm OD (gauge 21). This needle generates drops of about 2 mm in diameter.

The drops are projected onto a surface target (Parafilm) from a height of 50 cm which results in an impact speed of the drops of 3 m/s. Parafilm is used as a model surface in order to mimic the waxy cuticle of a leaf surface.

The droplet size is measured from the images captured by the camera by translating the number of pixels into millimeters. This was also confirmed from measurements of the mass of a known number of drops collected and weighed.

Deposition Control Agent

The deposition control agent is a derivatized guar gum having hydroxyalkyl grafts, and optionally other grafts.

Guar gum is the refined endosperm of the legume seed of *Cyamopsis tetragonolobus* (L.) Taub., a plant which physically resembles the soy plant. The gum is a pure food vegetable colloid recognized by the agricultural, chemical and food formulation industry for many years as having excellent thickening, film-forming and stabilizing properties.

Guar is often used in foods as a thickener and a binder of free water. In salad dressings, guar raises the viscosity of the emulsion and decreases the separation rate. Because guar functions to bind free water, it is used to stabilize foods such as ice cream by inhibiting the formation of ice crystals. Guar is also utilized to stabilize certain delicate, non-food emulsions such as 1:1 mixtures of water and mineral oil.

Guar has been shown to be useful as a lubricant not only by facilitating smooth extrusions at low pressures, but the additions of small amounts of guar have resulted in the reduction of frictional pressure drops in process water lines by up to 50%, thus increasing pump life and capacities and decreasing power requirements.

Functionally, guar is a cold water swelling, nonionic polysaccharide which develops and maintains its properties over a wide pH range. The guar polysaccharide is a complex carbohydrate polymer composed essentially of a straight chain of mannose units with single-membered galactose branches; chemically classified as a polygalactomannan.

Guar solutions or dispersions are simply prepared by rapidly sifting dry gum into a vigorously agitated tank of water and permitting the gum to hydrate. Higher water temperatures can shorten the hydration time so long as the heating is not so prolonged or excessive as to degrade the polymer.

At concentrations used in this invention, it is believed that solutions or dispersions of guar essentially have a zero yield value, i.e., they begin to flow at the slightest shear.

The nature of guar allows almost constant viscosity for a given solution concentration over the pH range of 3-10. Above pH 11, a lower viscosity results from the decreased ability of the gum to hydrate. The optimum hydration range occurs between pH 5 and 8. This unusual compatibility of guar over the 3-10 pH range is attributed to the nonionic nature of the molecule.

Etherification and esterification reactions can be made on the guar hydroxyl functionalities. The C6 hydroxyl position is the most reactive position for etherification, for example, with propylene oxide, but the secondary hydroxyls are also probable sites.

Principle etherification reactions are carboxymethylation via monochloroacetic acid, hydroxyalkylation via ethylene oxide or propylene oxide, and quaternization with various quaternary amine compounds containing reactive epoxide or chloride sites. Anionic and cationic sites modify the way the guar molecule interacts with inorganic salts, hydrated cellulosic and mineral surfaces, and organic particulates.

In general, the hydroxyalkyl ethers of polygalactomannans are prepared by reacting the polygalactomannans with alkylene oxides under basic conditions. In U.S. Pat. Nos. 3,723,408 and 3,723,409, guar flour is reacted with alkylene oxides in the presence of water and sodium hydroxide. The reaction product is then neutralized with acid, washed with an alcohol-water mixture, and is then dried and ground. In U.S. Pat. No. 3,483,121, the polygalactomannans and the alkylene oxides are reacted under basic conditions with small amounts of water and larger amounts of water miscible or water immiscible organic solvents.

Specific hydroxyalkylating agents include ethylene oxide, propylene oxide-1,2; butylene oxide-1,2; hexylene oxide-1,2; ethylene chlorohydrin; propylene chlorohydrin; and epichlorohydrin.

Hydroxypropylation increases the gum's solubility, resulting in a product which hydrates rapidly, regardless of water temperature. Hydroxyalkyl derivatives are more tolerant of the water-miscible solvents and thus can swell in and develop viscosity in aqueous solutions containing low molecular weight organic solvents such as methanol, ethanol, etc. Both hydroxyalkyl and carboxymethyl derivatives typically form clearer solutions than standard guar gum and also hydroxyalkyl derivatives resist thermal degradation better than standard guar. Hydroxypropyl guar is particularly useful as a flow modifier and friction reducing agent which does not flocculate solids.

Carboxyalkyl ethers and mixed carboxyhydroxyallyl ethers of polygalactomannans are described in U.S. Pat. Nos. 3,740,388 and 3,723,409, respectively. These derivatives are made by reacting the polygalactomannan with the derivatizing agents (halofatty acid and alkylene oxide) in a water-alcohol mixture followed by washing with water-alcohol mixtures.

Specific carboxyalkylating agents include chloroacetic acid, chloropropronic acid, and acrylic acid.

Carboxymethylation introduces an anionic function to the polymer chain and further increases the solubility of guar. Carboxymethyl hydroxypropyl guar is exceptional in its ability to suspend undissolved solids.

Other derivatives of polygalactomannans are described in such patents as U.S. Pat. No. 3,498,912 (quaternary ammonium alkyl ethers). In the described processes, the reactions are conducted in water-organic solvent mixtures and the reaction products are washed with solvents of water solvent mixtures.

Grafted guar derivatives may be formed by the use of grafting reactions, and these products may or may not also be derivatized using the methodologies herein described.

Specific quaternary ammonium alkylating agents are such agents as 2,3-epoxypropyl trimethylammonium chloride, 3-chloro-2-hydroxypropyl trimethylammonium chloride and the like.

The term "derivatized guar" is meant to include any of the above described derivatized guar products.

Guar, derived from a nitrogen-fixing, renewable resource, is a versatile, environmentally friendly, highly biodegradable polymer. Derivatized guars are slightly less sensitive to biological degradation, as the molecules are less suitable as food for common organisms.

The deposition control derivatized guar advantageously has a molecular weight of from 50,000 g/mol to 10,000,000 g/mol, preferably of from 200,000 g/mol to 5,000,000 g/mol and more preferably of from 1,000,000 g/mol to 5,000,000 g/mol.

Examples of derivatized guars suitable for the invention include the following:

Jaguar™ 8012, marketed by Rhodia, a hydroxypropyl guar having a molecular substitution of about 1.2, Jaguar HP-105, marketed by Rhodia, a hydroxypropyl guar having a molecular substitution of about 0.6, Jaguar HP-140, marketed by Rhodia, a hydroxypropyl guar having a molecular substitution of about 0.6, and Jaguar 8079, marketed by Rhodia, a hydroxypropyl guar having a molecular substitution of about 0.8.

Amount of Deposition Control Agent

The amount of deposition control agent in the spray composition is advantageously of from 0.001 to 2% by weight, preferably of from 0.01 to 0.5% by weight, more preferably of from 0.01 to 0.1% by weight. Is it believed that the higher the molecular substitution is, and/or the higher the number of carbon atoms in hydroxyalkyl groups is, the better the anti-rebound effect is, and/or the lower the amount of the derivatized guar is needed.

Thus, the spray composition is advantageously such that the deposition control agent is hydroxypropyl guar having a molecular substitution of at least 0.6, preferably of at least 0.8, more preferably of at least 1.1, and even more preferably of at least 1.3, and the amount thereof is of from 0.001 to 2% by weight, preferably of from 0.01 to 0.5% by weight, more preferably of from 0.01 to 0.1% by weight, or the deposition control agent is hydroxybutyl guar having a molecular substitution of at least 0.15, 0.001 to 1% by weight, preferably of from 0.01 to 0.5% by weight, more preferably of from 0.01 to 0.05% by weight.

Performance

Performance can be measured by comparing the retraction speed of the drops (as defined above), where a polymer giving a lower retraction speed has a lower tendency to rebound. The critical retraction speed for rebound might depend on the characteristics of the impact, including the drop size, impact velocity and additives. By keeping the drop size and impact velocity constant, the effect of the added deposition control agent can be evaluated through comparing the retraction speeds of the drops. A performance of one deposition control agent is thereby compared with another.

The composition, the surfactant, the amount thereof, the deposition control agent, and/or the amount thereof are preferably such that the retraction speed is of lower than 200 mm/s.

Surfactant

The spray composition comprises at least one surfactant. The surfactant usually helps in formulating the active ingredient in the spray composition. However the surfactant might modify the affinity of the composition for the surface of the target, for example a leaf. Without being bound to any theory it is believed that invention is at least partly connected to controlling the affinity modification.

Various surfactants, or combinations of surfactants, can be present in the composition. The surfactants include anionic, nonionic, cationic, amphoteric, and zwitterionic surfactants, and mixtures thereof.

Anionic surfactants that are suitable for the spray composition according to the invention include:

phosphoester surfactants;

alkylsulphonic acids, arylsulphonic acids, possibly substituted with one of more hydrocarbon-containing groups, wherein the acid function is partially or completely in the salt form, such as $C_8$-$C_{50}$ alkylsulphonic acids, more particularly $C_8$-$C_{30}$, preferably $C_{10}$-$C_{22}$, benzenesulphonic acids, naphthalenesulphonic acids, substituted with one to three $C_1$-$C_{30}$ alkyl groups, preferably $C_4$-$C_{16}$, and/or $C_2$-$C_{30}$, preferably $C_4$-$C_{16}$ alkenyl;

mono- or di-esters of alkylsulphosuccinic acids, wherein the linear or branched alkyl portion may be substituted by one or more linear or branched $C_2$-$C_4$ hydroxyl and/or alkoxyl groups (preferably ethoxylated, propoxylated, ethopropoxylated);

phosphate esters, more particularly selected from those comprising at least one saturated, unsaturated or aromatic, linear or branched hydrocarbon group containing 8 to 40 carbon atoms, preferably 10 to 30, possibly substituted by at least one alkoxylated group (ethoxylated, propoxylated, ethopropoxylated) (Further, they comprise at least one phosphate ester group, mono- or di-esterified such that it is possible to have one or two acid groups that are free or completely or partially in the salt form. Preferred phosphate esters are of the following type: alkoxylated (ethoxylated and/or propoxylated) mono- or di-esters of phosphoric acid and: mono-, di- or tri-styrylphenol, or mono-, di- or tri-alkylphenol, possibly substituted by one to four alkyl groups; or a $C_8$-$C_{30}$ alcohol, preferably $C_{10}$-$C_{22}$; or non-alkoxylated mono- or di-esters of phosphoric acid and a $C_8$-$C_{22}$ alcohol, preferably $C_{10}$-$C_{22}$);

sulphate esters obtained from saturated or aromatic alcohols, possibly substituted by one or more alkoxylated groups (ethoxylated, propoxylated, ethopropoxylated), and for which the sulphate functions are in the form of the free acid or are partially or completely neutralized (Examples that can be cited are sulphate esters, more particularly obtained from saturated or unsaturated $C_8$-$C_{20}$ alcohols, which may contain 1 to 8 alkoxylated groups (ethoxylated, propoxylated, ethopropoxylated));

sulphate esters obtained from polyalkoxylated phenol, substituted by 1 to 3 saturated or unsaturated $C_2$-$C_{30}$ hydroxycarbon-containing groups, and in which the number of alkoxylated motifs is in the range 2 to 40;

sulphate esters obtained from polyalkoxylated mono-, di- or tri-styrylphenol in which the number of alkoxylated motifs is in the range 2 to 40; and oleoyltaurate salts.

It should be noted that in the case where the compounds are partially or completely in the salt form, the counter-ion can be an alkali metal such as sodium or potassium, or an ammonium ion with formula $N(R)_4^+$ where R, which may be identical or different, represents a hydrogen atom or a $C_1$-$C_4$ alkyl radical which may be substituted by an oxygen atom.

Nonionic surfactants that are suitable for the spray composition according to the invention include:

polyalkoxylated (ethoxylated, propoxylated, ethopropoxylated) phenols substituted by at least one $C_4$-$C_{20}$ alkyl radical, preferably $C_4$-$C_{12}$, or substituted by at least one alkylaryl radical wherein the alkyl portion is $C_1$-$C_6$ (More particularly, the total number of alkoxylated motifs is in the range 2 to 100. Examples that can be cited are polyalkoxylated mono-, di- and tri-(phenylethyl) phenols or polyalkoxylated nonylphenols);

$C_6$-$C_{22}$ fatty alcohols or acids that may be polyalkoxylated (ethoxylated, propoxylated, ethopropoxylated). When present, the number of alkoxylated motifs is in the range 1 to 60 (The term "ethoxylated fatty acid" includes both products obtained by ethoxylation of a fatty acid by ethylene oxide and those obtained by esterification of a fatty acid by a polyethylene glycol);

polyalkoxylated (ethoxylated, propoxylated, ethopropoxylated) triglycerides of plant or animal origin. (The following are suitable: triglycerides from lard, tallow, peanut oil, butter oil, cottonseed oil, linseed oil, olive oil, palm oil, grapeseed oil, fish oil, soya oil, castor oil, rapeseed oil, coprah oil, coconut oil, and with a total number of alkoxylated motifs in the range 1 to 60. The term "ethoxylated triglyceride" encompasses both products obtained by ethoxylation of a triglyceride by ethylene oxide and those obtained by transesterification of a triglyceride using a polyethylene glycol);

polyalkoxylated (ethoxylated, propoxylated, ethopropoxylated) sorbitan esters, more particularly esters of sorbitol cyclized with $C_{10}$ to $C_{20}$ fatty acids such as lauric acid, stearic acid or oleic acid, and with a total number of alkoxylated motifs in the range 2 to 50;

alkylpolyglucosides;

silicone based surfactants;

ethoxypropoxy copolymers; and ethoxy and ethoxypropoxy fatty amines and/or ether amines.

Amphoteric or zwitterionic surfactants that are suitable for suitable for the spray composition according to the invention include:

betaines, such as sulfobetaines (sultaines), carboxybetaines (regular betaines), phosphobetaines, preferably alkylbetaines or alkylamidobetaines, for examples compounds having one or more of the following formulae:

$R^1R^2R^2N^+—CH_2COO—$ (I)

$R^1R^3HN^+—CH_2—CH_2COO—$ (II)

(III)

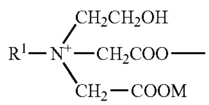

(IV)

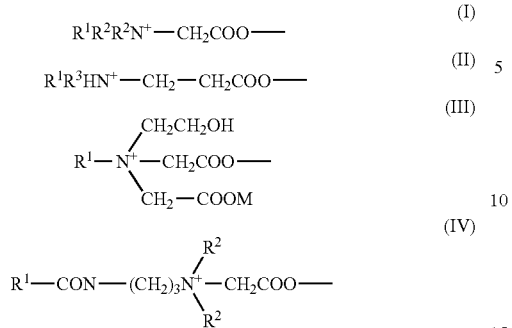

in which formulae:
- $R^1$ represents a linear or branched alkyl group containing 3 to 30 carbon atoms, preferably 3 to 20 carbon atoms, such as propyl, decyl, dodecyl, tetradecyl, hexadecyl, tetrahexadecyl, octyl, or mixtures thereof, or an alkamide group, such as dodecanamide;
- $R^2$, which may or may not be identical, represent an alkyl radical, preferably a methyl radical;
- $R^3$ represents a hydrogen atom or a $—CH_2COOM$ radical or an alkyl radical;

M represents an alkali metal, preferably sodium,
alkylamidoamphoacetates,
alkylamphoacetates, and
amine oxides, optionally poly alkoxylated.

The concentration of surfactant present in the spray composition can be of at least twice the critical micellar concentration in water. One skilled in the art knows how to measure the critical micellar concentration. These data are also available in literature, for example in "Industrial Utilization of Surfactants" by Manilal Dahanayake and Milton J. Rosen (AOCS Press).

The spray composition preferably comprises at least 0.01% by weight of surfactant, and preferably less than 5% by weight, more preferably between 0.05% by weight and 2% by weight, wherein these amount relative to the total amount of surfactants in the composition (mixture of surfactants).

Active Ingredient

The active ingredient is preferably an agrochemical active ingredient. By agrochemical active ingredient it is meant a compound having an effect on a plant growth, whether by killing undesired organisms or avoiding development thereof, or by directly having an effect on the plant. The active ingredient can be an herbicide, a pesticide, a fungicide, an aphicide, a miticide, a fertilizing agent or a compound having another action.

Examples of active ingredients include:

- insecticides, for example selected from the group consisting of carbamates, such as methomyl, carbaryl, carbofuran, or aldicarb; organo thiophosphates such as EPN, isofenphos, isoxathion, chlorpyrifos, or chlormephos; organo phosphates such as terbufos, monocrotophos, or terachlorvinphos; perchlorinated organics such as methoxychlor; synthetic pyrethroids such as fenvalerate, abamectin and emamectin benzoate, Neonicotinoides such as thiamethoxam or imidacloprid; pyrethroids such as lambda-cyhalothrin, cypermethrin or bifenthrin, and oxadiazines such as indoxacarb, Imidachlopryd, Fipronil;
- nematicide carbamates, such as oxamyl;
- herbicides, for example selected from the group consisting of triazines such as metribuzin, hexaxinone, or atrazine; sulfonylureas such as 2-chloro-N-[(4-methoxy-6-methyl-1,3,5-triazin-2-yl)aminocarbonyl]-benzenesulfonamide; uracils (pyrimidines) such as lenacil, bromacil, or terbacil; ureas such as linuron, diuron, siduron, or neburon; acetanilides such as alachlor, or metolachlor; thiocarbamates such as benthiocarb (SATURN), triallate; oxadiazol-ones such as oxadiazon; phenoxyacetic acids such as 2,4-D; diphenyl ethers such as fluazifop-butyl, acifluorfen, bifenox, or oxyfluorfen; dinitro anilines such as trifluralin; glycine phosphonates such as glyphosate salts and esters; dihalobenzonitriles such as bromoxynil, or ioxynil, dipyridiliums such as paraquat; dims such as chlethodim; fops such as fluazifop;
- fungicides, for example selected from the group consisting of nitrilo oximes such as cymoxanil (curzate); imidazoles such as benomyl, carbendazim, or thiophanate-methyl; triazoles such as triadimefon; sulfenamidessuch as captan; dithio-carbamates such as maneb, mancozeb, or thiram; chloronated aromatics such as chloroneb; dichloro anilines such as iprodione, strobilurins such as kresoxim-methyl, trifloxystrobin or azoxystrobin; Chlorothalonil; Copper salts such as Copper oxychloride; Sulfur; Phenylamides and derivatives such as Metalaxyl or mefenoxam;
- aphicides, for example selected in the group consisting of carbamates, such as pirimicarb;
- miticides, for example selected in the group consisting of propynyl sulfites such as propargite; triazapentadienes such as amitraz; chlorinated aromatics such as chlorobenzilate, or tetradifan; dinitrophenols such as binapacryl; and
- foliar fertilizers that provide, for example nitrogen, potassium, phosphorus micronutrients, and other elements necessary for plant growth.

The spray compositions comprising agrochemical active can further comprise the following ingredients:

- a further drift control agent,
- an anti-foaming agent,
- an anti-leaching agent,
- a rheology modifier, such as glycol and ethylene glycol,
- a humectant, such as glycerine or glycol,
- a fluid fertilizer, such as 30-0-0,
- penetrants and/or spreading agents, such as silicones, vegetable or petroleum oils, solvents, methylated seed oils,
- chelators and water conditioners, such as citric acid, EDTA and inorganic salts like ammonium sulfate, ammonium phosphate and urea, and/or
- acrylates and methacrylates polymers.

According to other embodiments, the spray composition is:

- a coating composition, the active ingredient being at least one ingredient of the coating to be deposited on a surface, for example a paint, or a coil-coating, or any other industrial coating or surface treatment, onto surfaces including polymeric films, metal coils, metal parts, glass panels, paper, etc. (In these application, controlling the deposition can help in avoiding misting);
- a textile-care composition, the active ingredient being at least one ingredient to be deposited on a textile surface, for example protective membranes, etc.;

a hard surface cleaning composition, the active ingredient being at least one ingredient to be applied to a hard surface;

an ink, a color coating or a stain coating, for example provided by ink-jet printers; or an aerosol spray, for example insecticidal, fungicidal, anti-microbial or disinfecting formulations dispensed from canisters.

Spraying the Composition

The composition, advantageously the compositions comprising an agricultural active ingredient, can be ground sprayed, aerial spread or discharged in droplets. This is advantageously performed though a nozzle, and the droplets preferably have a size of at least 50 μm, preferably of at least 150 μm, and of less than 5 mm, preferably of less than 2 mm.

Some details or advantages of the invention will appear in the non-imitative examples below.

EXAMPLES

The following ingredients were used in the Examples:
water,
surfactant: an anionic, dodecyl-tridecyl alcohol ethoxylated with nine moles of ethylene oxide, phosphoester surfactant, provided by Sasol (hereafter referred to as "anionic phosester"),
deposition control agent 1: Jaguar 8012, marketed by Rhodia, a hydroxypropyl guar having an ms of about 1.2, and a weight average molecular weight of about 1.97 million,
deposition control agent 2 (or HBGO90): a hydroxybutyl guar having an ms of about 0.9, and a peak molecular weight (molecular weight at highest point in chromatogram) of about 2.4 million,
deposition control agent 3 (comparative): Jaguar 8000, marketed by Rhodia, a hydroxybutyl guar having an ms of about 0.4, and a weight molecular weight of about 2.3 million, and
deposition control agent 4: Jaguar 8021, developed by Rhodia, a hydroxypropyl guar having an ms of about 1.9, and a molecular weight of between 2 and 4 million.

Preparation of Samples:

A. The preparation procedure for the polymer stock solution was:
weigh approximately 200 g of deionised water in a bottle with a magnetic stirrer,
weigh 0.6000 g of deposition control agent in a plastic cup,
add the deposition control agent in the bottle of water while stirring vigorously,
fill to 300 g with deionised water,
stir under magnetic stirrer for 2 hours,
leave overnight on rollers,
adjust the pH of the stock solution to 7.0±0.2 with HCl 0.1N and NaOH 0.1 N, and
store the solution at 5.0° C.

B. The solutions containing only the deposition control agents are adjusted to have the same surface tension in order to isolate the effect of the deposition control agent only. Preparation of the solutions for drop impact experiments containing the deposition agents is described below (compositions 1C, 2C and 6C in table below):
weigh 30 g of the 0.2% stock solution in a bottle,
add butanol in order to bring the surface tension to 62.0±0.3 mN/m,
fill to 100 g with deionised water, and
leave on rollers for one hour.

C. The solutions containing both the deposition control agents and anionic phosester are prepared as described below (compositions 3, 4, 5C, 7C, 8 in table below):

1. preparation of 20*CMC anionic phosester solution:
   1 g of the anionic phosester was weighed,
   dissolve the surfactant in deionised water to obtain a total weight of 100 g,
   shake manually the solution at 20*CMC and homogenize on the rollers for ½ hour, and
   store at room temperature.

2. Preparation of Buffer at pH=5.0:
   weigh 20.42 g of potassium hydrogen phthalate in a bottle,
   fill to 100 g with deionised water to obtain a 0.1 M solution,
   homogenize the solution on the Roller for ½ hour,
   weigh 4 g of sodium hydroxide (NaOH) in a beaker,
   weigh 996 g of deionised water in a bottle and add NaOH to obtain a 0.1 M solution,
   homogenize the solution on the Roller for ½ hour,
   mix both solutions in the proportion of 50 ml of the 0.1M solution of potassium hydrogen phthalate with 22.6 ml of 0.1M solution of sodium hydroxide,
   homogenize the buffer and check that pH is equal to 5.0±0.2, and
   store the buffer at 5.0° C.

3. Preparation of 0.06% deposition control aid solution+ 2*CMC anionic phosester buffered at pH=5.0:
   weigh 30 g of 0.2% polymer stock solution prepared in A,
   add 10 g of 20*CMC surfactant solution prepared in B(1),
   fill to 100 g with the buffer prepared in B(2),
   homogenize the solution on the roller for 1 hour, and
   store at 5.0° C.

The following compositions are prepared (amounts in weight %). C stands for comparative):

| | 1C | 2C | 3 | 4 | 5C | 6C | 7 | 8 |
|---|---|---|---|---|---|---|---|---|
| Surfactant | 0 | 0 | 0.1 | 0.1 | 0.1 | 0 | 0.1 | 0.1 |
| Deposition control agent 1 | 0.06 | | 0.06 | / | / | / | / | |
| Deposition control agent 2 | / | 0.06 | / | 0.06 | / | / | / | |
| Deposition control agent 3 (comparative) | / | / | / | / | 0.06 | 0.06 | | |
| Deposition control agent 4 | | | | | | | | 0.06 |
| Retraction Speed (mm/s) | 15.1 | 30.4 | 169.9 | 68.3 | 489 | 36.5 | 213.2 | 55.9 |

Impact Test

The drop impact experiment is carried out as follows. The underside of a strip of parafilm of 6.0 cm×2.5 cm is carefully stuck to a glass plate by wetting the plate with a water spray. Any scratch, compression or contamination of the surface is avoided by keeping the protective layer of the parafilm in place. The protective film on the upper side is then carefully removed just prior to impacting a drop. Fluid is fed to the needle and the formed drop falls under gravity from a height of 50 cm onto the above described surface. The Phantom 5 high-speed camera captures the images of the falling drop and its impact on the surface. The images are then analysed for the drop size and impact speed. The drop impact speed is measured by knowing the number of pixels in the image that corresponds to 1 mm, and knowing the frame capture rate (typically 1000 frame per second).

Figure 3:
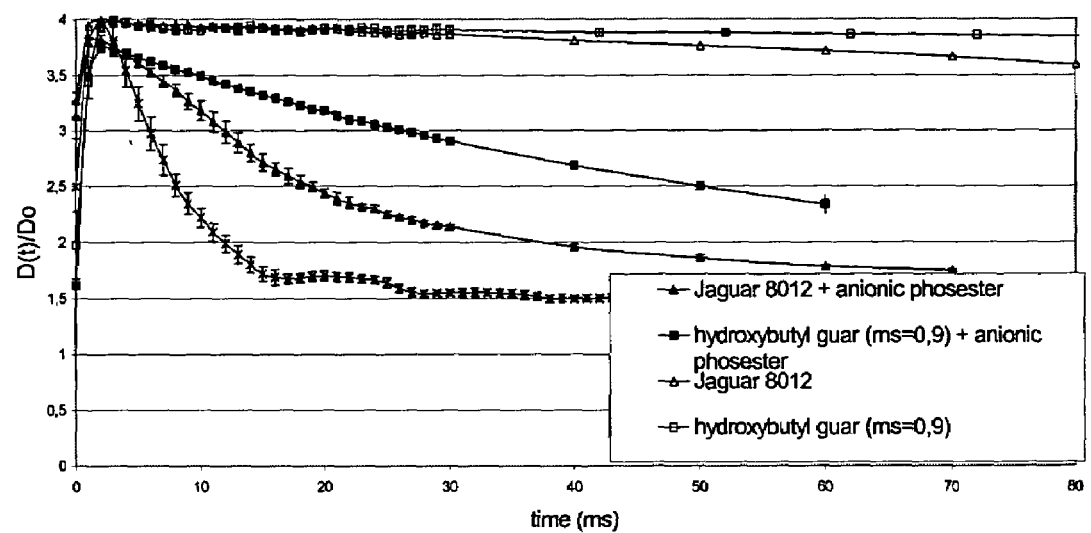
FIG. 3 shows test results for compositions of Examples 1C to 5C.
Figure 4:
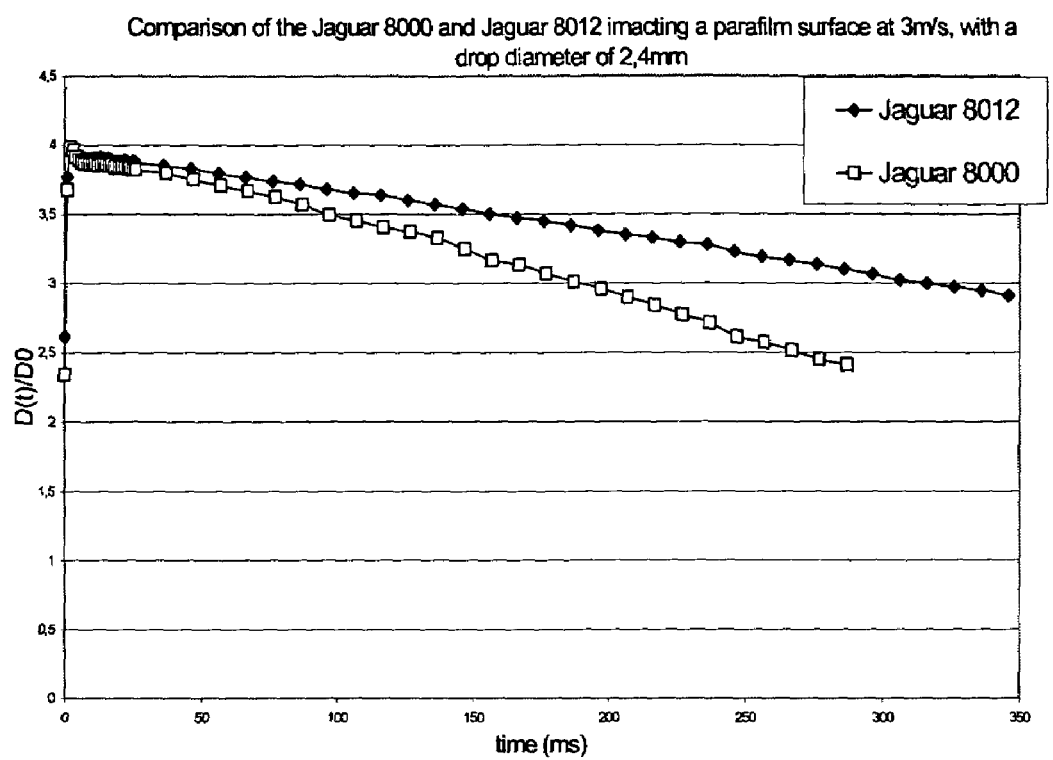
FIG. 4 shows test results for compositions of Examples 1C and 6C.
Figure 5:
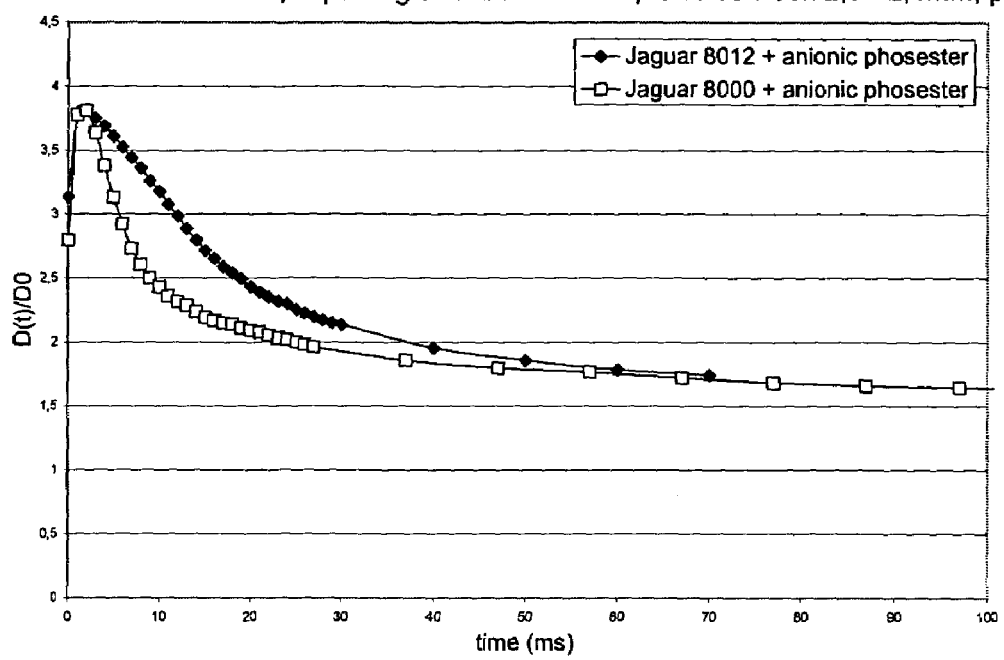
FIG. 5 shows test results for compositions of Examples 3 and 7C.
Figure 6:
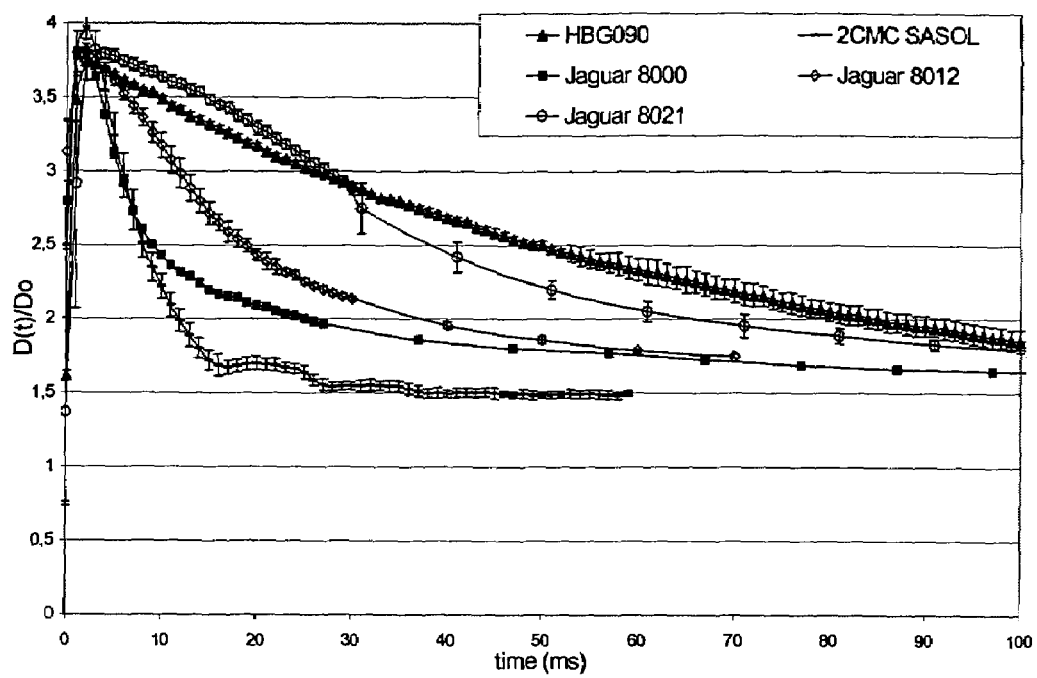
FIG. 6 shows test results for compositions of Examples 3, 4, 5C, 6C and 8.

FIG. 3 shows results for compositions 1C to 5C.
FIG. 4 shows results for compositions 1C and 6C.
FIG. 5 shows results for compositions 3 and 7C.
FIG. 6 shows results for compositions 3, 4, 5C, 6C and 8.

The invention claimed is:

1. A spray composition, comprising:

an aqueous spray medium, between 0.05% by weight and 2% by weight of at least one surfactant, and from 0.01 to 0.5% by weight of a deposition control agent, wherein the deposition control agent is selected from the group consisting of hydroxypropyl guars having a molecular substitution of at least 1.1 and hydroxybutyl guars having a molecular substitution of at least 0.4.

2. A spray composition according to claim 1, wherein the surfactant is an anionic surfactant, a cationic surfactant, a nonionic surfactant, an amphoteric surfactant, a zwitterionic surfactant, or a mixture thereof.

3. A spray composition according to claim 1, wherein the deposition control agent has a weight average molecular weight of from 50,000 g/mol to 10,000,000 grams per mole.

4. A spray composition according to claim 1, having a retraction speed of lower than 200 mm/s.

5. A spray composition according to claim 1, further comprising an active ingredient, wherein the active ingredient is a herbicide, a pesticide, a fungicide, an aphicide, a miticide, or a fertilizing agent.

6. A spray composition according to claim 5, wherein the active ingredient is a fungicide selected from the group consisting of nitrilo oximes; imidazoles; triazoles; sulfenamides; dithio-carbamates; strobilurins; Chlorothalonil; copper salts; sulfur; phenylamides and phenylamide derivatives and chloronated aromatics.

7. A spray composition according to claim 5, wherein the active ingredient is a foliar fertilizer.

8. A spray composition according to claim 5, wherein the composition further comprises one or more of:

a further drift control agent, an anti-foaming agent, an anti-leaching agent, a rheology modifier, a humectant, a fluid fertilizer;

penetrants and/or spreading agents, and chelators and water conditioners.

9. A spray composition according to claim 1, wherein the composition is:

a coating composition, further comprising an active ingredient to be deposited on a surface, a textile-care composition, further comprising an active ingredient to be deposited on a textile surface, a hard surface cleaning composition, further comprising an active ingredient to be applied to a hard surface, an ink, a color coating or stain coating, or an aerosol spray to be dispensed from a canister.

10. A method of controlling the deposition of a composition comprising an active agent, comprising the step of:

preparing a spray composition according to claim 5, and ground or aerial spraying or discharging droplets of the composition.

11. A method according to claim 10, wherein spraying is performed though a nozzle, and the droplets have size of at least 50 μm.

12. The spray composition of claim 1, wherein the deposition control agent is a hydroxypropyl guar.

13. The spray composition of claim 12, wherein the hydroxypropyl guar has a molecular substitution of at least 1.3.

14. The spray composition of claim 1, wherein the deposition control agent is a hydroxybutyl guar.

15. The composition of claim 1, wherein the composition exhibits improved anti-rebound properties.

* * * * *